United States Patent [19]

Andrews et al.

[11] Patent Number: 5,093,334
[45] Date of Patent: Mar. 3, 1992

[54] DERMAL TREATMENT OF WORM DISEASES IN CATS WITH PRAZIQUANTEL

[75] Inventors: Peter Andrews, Wuppertal; Herbert Voege, Leverkusen, both of Fed. Rep. of Germany

[73] Assignee: Bayer Aktiengesellschaft, Leverkusen, Fed. Rep. of Germany

[21] Appl. No.: 556,590

[22] Filed: Jul. 20, 1990

Related U.S. Application Data

[60] Division of Ser. No. 398,202, Aug. 24, 1989, Pat. No. 4,988,696, which is a continuation of Ser. No. 101,899, Aug. 28, 1987, abandoned.

[30] Foreign Application Priority Data

Oct. 11, 1986 [DE] Fed. Rep. of Germany ....... 3634755

[51] Int. Cl.$^5$ .................... A61K 31/495; A61K 31/50
[52] U.S. Cl. .................................... 514/250; 514/947
[58] Field of Search ................................. 514/947, 250

[56] References Cited

U.S. PATENT DOCUMENTS 4,695,465  9/1987  Kigasawa et al. ................. 514/947

OTHER PUBLICATIONS

The Merck Index 10th ed. (1983) p. 749.
Thomas et al. Research in Vet. Sci. (1978) 24, 20-25.

Primary Examiner—Frederick E. Waddell
Assistant Examiner—Raymond J. Henley, III
Attorney, Agent, or Firm—Sprung Horn Kramer & Woods

[57] ABSTRACT

A method of treating a worm disease in a cat which comprises dermally applying to the cat 0.1-5 mg of praziquantel per kg of body weight.

1 Claim, No Drawings

DERMAL TREATMENT OF WORM DISEASES IN CATS WITH PRAZIQUANTEL

This is a division of application Ser. No. 07/398,202, filed 8/24/89 now U.S. Pat. No. 4,988,696 which is a continuation of Ser. No. 07/101,899, filed 8/28/87, now abandonded.

The present invention relates to the dermal use of praziquantel for combating worm diseases in cats and agents suitable for this application.

It is known that praziquantel can be used for combating worm diseases in animals, for example dogs and cats (U.S. Pat. No. 4,113,867; P. Andrews et al. Medicinal Research Rev. Vol. 3(2) 147-200 (1983)). Treatment of dogs and cats is by oral or parenteral administration of the active compound in doses of about 5 mg/kg of body weight. Oral treatment, in which the active compound is administered directly into the habitat of the parasite, is preferred. A very good activity in low doses can therefore be expected with this type of administration.

A significantly poorer activity must be expected if the active compound is administered dermally. This is also generally known (Herlich et al. Veterinary Med. 56, pages 219-221 (1961); Hotson et al. Australian Vet. J. 39; pages 108-115 (1963)). Investigations with praziquantel on rats show that higher active compound doses are required both with dermal and with subcutaneous administration of praziquantel than with oral administration (H. Thomas et al. Z. Parasitenkd. 52; 117-127 (1977).

In investigations against Schistosoma mansoni in mice, it was found that on oral administration of the active compound only one tenth of the amount administered dermally was required to achieve the same action (R. Gönnert et al. Z. Parasitenkd. 52; pages 129-150 (1977)).

It was likewise found in investigations against Taenia hydatigena in dogs that the dermal use form gave only unsatisfactory results. A dose of 1 mg/kg is recommended for oral use. The dermal use of a solution of the active compounds in isopropanol at a dose of 5 mg/kg showed an action in only one out of two dogs (H. Thomas et al. Research Vet. Sci. 24; pages 20-25 (1978)).

It was therefore to be expected that on dermal use of praziquantel higher doses (about 10 times higher) are required than with oral use.

However, in addition to activity, dermal agents must also fulfil certain expectations of the user. Even after application, the coat of the animal should not look wet or feel damp. In addition, the amount of solvent to be used must be kept as low as possible in order to avoid harmful effects of the solvent on the animal. The amount of solvent used should therefore not exceed 0.1 ml/kg of cat live weight. It has scarcely been posible to find solvents which are harmless to cats and which dissolve the amount of praziquantel required for activity. This was one reason why there are as yet no agents which contain praziquantel and can be used dermally on cats.

It has now been found that praziquantel can be used for dermal combating of worm diseases in cats in application amounts of 0.1-5 mg per kg of body weight.

Agents for dermal combating of worm diseases in cats have been found which contain praziquantel in concentrations of 0.1-20 percent by weight. It has been found that these agents must be administered to cats in amounts of 0.01-0.5 ml/kg of cat live weight for combating worm diseases.

It was surprising that worm diseases in cats can be combated successfully with this treatment. Surprisingly, in contrast to the statements from the prior art, the amount of praziquantel which is also required for oral use is sufficient for dermal treatment of cats. In spite of the requirement of using small amounts of solvents, sufficient amounts of active compound can thus be applied to the cats.

The advantage of dermal use is obvious. The animal does not have to be held before the treatment, as is necessary in the case of administration as an injection. It also does not have to be treated with medicated food, where there is the risk of refusal of food. Simple application of drops of the formulation to the animal, for example between the shoulder blades, in order to avoid the animal licking the agent off its coat, is sufficient.

As a result of the small amount of active compound which is used, solvents in which sufficient amounts of active compound are dissolved and which neither irritate the skin of the animal nor harm the animal if it licks the agent off its coat can be selected.

Praziquantel, the common name for 2-(cyclohexylcarbonyl)-1,2,3,6,7,11-b-hexahydro-4 H-pyrazino[2,1-a]-isoquinolin-4-one, is known.

As already mentioned, praziquantel is used in the process according to the invention in application amounts of 0.1-5 mg, preferably 1-5 mg and particularly preferably about 1 mg per kg of body weight.

The agents according to the invention contain 0.1-20, preferably 1-5 and particularly preferably about 1 percent by weight of praziquantel, in addition to solvents and if appropriate other auxiliaries.

The agents according to the invention are employed in amounts of 0.01-0.5 ml, preferably 0.1-0.5 ml and particularly preferably about 0.1 ml per kg of live weight of the cats.

The agents according to the invention are sprayed on, applied dropwise, dripped on or misted on to limited areas of the coat of the cat. Areas on the animal from which the agent cannot be licked off without difficulty are preferably treated.

The agents according to the invention are prepared by dissolving, suspending or emulsifying the active compound in suitable solvents or solvent mixtures which are tolerated by the skin. If appropriate, other auxiliaries, such as dyestuffs, absorption-promoting substances, antioxidants, light stabilizers or adhesives, are added.

Solvents which are particularly suitable for the preparation of the agents according to the invention are:

Alkanols, such as ethyl alcohol, isopropyl alcohol, n-butyl alcohol and amyl alcohol.

Glycols, such as propylene glycol, glycerol, 1,3-butylene glycol, polyethylene glycols and polypropylene glycols.

Aromatic alcohols, such as benzyl alcohol, phenylethanol and phenoxy ethanol.

Trihydric alcohols, such as glycerol.

Carboxylic acid esters, such as, for example, ethyl acetate, benzyl benzoate, butyl acetate and ethyl lactate.

Aromatic and/or aliphatic hydrocarbons.

Oils, such as, for example, cottonseed oil, groundnut oil, corn core oil, olive oil, castor oil, sesame oil and synthetic analogues of these oils.

Water.

Ketones, such as, for example, acetone and methyl ethyl ketone.

Ethers, such as alkylene glycol alkyl ethers, dipropylene glycol monomethyl ether and diethylene glycol monobutyl ether.

Furthermore dimethylformamide, dimethylacetamide, N-methylpyrrolidone and 2-dimethyl-4-oxymethylene-1,3-dioxolane.

The agents according to the invention can also contain emulsifiers and wetting agents, such as, for example, anionic surfactants, such as, for example, Na lauryl sulphate, fatty alcohol ether-sulphates and the monoethanolamine salt of mono/dialkyl polyglycol etherorthophosphoric acid esters; cationic surfactants, such as, for example, cetyltrimethylammonium chloride; ampholytic surfactants, such as, for example, di-Na N-lauryl-$\beta$-iminodipropionate and lecithin; non-ionic surfactants, such as, for example, polyoxyethylated castor oil, polyoxyethylated sorbitan monooleate, sorbitan monostearate, glycerol monostearate, polyoxyethylene stearate and alkylphenol polyglycol ethers.

The agents according to the invention can also contain absorption-promoting substances, such as, for example, dimethylsulphoxide. They can furthermore contain spreading oils. The spreading oils include, inter alia: silicone oils of varying viscosity, fatty acid esters, such as ethyl stearate, di-n-butyl adipate, hexyl laurate, dipropylene glycol pelargonate, esters of a branched fatty acid of medium chain length with saturated $C_6$-$C_{18}$ fatty alcohols, isopropyl myristate, isopropyl palmitate, caprylic/capric acid esters of saturated fatty alcohols of $C_{12}$-$C_{18}$ chain length, isopropyl stearate, oleyl oleate, decyl oleate, ethyl oleate, ethyl lactate, dibutyl phthalate, diisopropyl adipate, triglycerides, such as caprylic/capric acid triglyceride, triglyceride mixtures with vegetable fatty acids of $C_8$-$C_{12}$ chain length or other specially selected natural fatty acids, partial glyceride mixtures of saturated or unsaturated fatty acids which optionally also contain hydroxyl groups, mono- and diglycerides of $C_8$/$C_{10}$ fatty acids and others.

Fatty alcohols, such as isotridecyl alcohol, 2-octyldodecanol, cetylstearyl alcohol and oleyl alcohol.

Fatty acids, such as, for example, oleic acid.

Other auxiliaries which may be mentioned are: adhesion promoters, for example carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, paraffins, oils, waxes and colloidal silicic acid; dyestuffs which are permitted for use on animals; antioxidants, such as, for example, sulphites or metabisulphites, such as potassium metabisulphite, ascorbic acid, butylhydroxytoluene, butylhydroxyanisole and tocopherol; and light stabilizers, for example from the benzophenone or novantisolic acid class.

The agents according to the invention can be used against all the parasitic tapeworms in cats. These include Hydatigera taeniaeformis
Dipylidium canium
Joyeuxiella pasquali
Echinococcus multilocularis They are particularly preferably used against Hydatigera taeniaeformis.

Examples of the agents according to the invention which may be mentioned are the agents with the following compositions:

| Example 1 | |
|---|---|
| Praziquantel | 20 g |
| Benzyl alcohol | to 100 ml |
| Example 2 | |
| Praziquantel | 20 g |
| Isopropyl myristate | 5 g |
| Benzyl alcohol | to 100 ml |
| Example 3 | |
| Praziquantel | 10 g |
| Ethyl lactate | to 100 ml |
| Example 4 | |
| Praziquantel | 10 g |
| Isopropyl myristate | 5 g |
| Ethyl lactate | to 100 ml |
| Example 5 | |
| Praziquantel | 10 g |
| Isopropyl myristate | 5 g |
| N-Methylpyrrolidone | to 100 ml |
| Example 6 | |
| Praziquantel | 10 g |
| Dimethylsulphoxide (DMSO) | 20 g |
| Benzyl alcohol | to 100 ml |
| Example 7 | |
| Praziquantel | 10 g |
| Benzyl alcohol | to 100 ml |
| Example 8 | |
| Praziquantel | 20 g |
| Benzyl alcohol | 43.9 g |
| Benzyl benzoate | 43.9 g |
| Example 9 | |
| Praziquantel | 1 g |
| Isopropyl myristate | 5 g |
| Benzyl alcohol | 97.04 g |
| Example 10 | |
| Praziquantel | 1 g |
| Isopropyl myristate | 5 g |
| N-Methylpyrrolidone | 96.19 g |
| Example 11 | |
| Praziquantel | 1 g |
| DMSO | 30 g |
| N-Methylpyrrolidone | 73.97 g |

EXAMPLE A

In Vivo Tapeworm Test

Taenia taeniaeformis—Cats

Cats infected experimentally with Taenia taeniaeformis are treated once 6 weeks after the infection by applying to the skin between the neck and the shoulder blades the agent in an amount such that the stated dose of active compound is achieved. The number of tapeworms excreted in the faeces deposited 0–48 hours after treatment is determined. 6 weeks after the first treatment, a treatment which is known to be fully effective is administered and the faeces are then examined to investigate whether tapeworms have survived the first treatment. If no tapeworms have survived the first treatment, the first treatment was fully effective. The agent and the dose of active compound, in mg/kg of cat live weight, required for full activity are shown in the following table.

| Agent according to Example | Fully effective dose of active compound in mg/kg |
|---|---|
| 2 | 1 |
| 5 | 1 |
| 8 | 1 |
| 11 | 1 |

It is understood that the specification and examples are illustrative but not limitative of the present invention and that other embodiments within the spirit and scope of the invention will suggest themselves to those skilled in the art.

We claims:

1. A composition for treating a worm disease in an animal comprising praziquantel dissolved, suspended or emulsified in a concentration of about 1 to 5% in a skin-tolerated solvent consisting of a mixture of N-methylpyrrolidone and isopropyl myristate.

* * * * *